(12) United States Patent
Wu

(10) Patent No.: US 7,762,987 B2
(45) Date of Patent: Jul. 27, 2010

(54) SAFETY SYRINGE DEVICE WITH SEPARABLE NEEDLE STEM BY TURNING BACK

(76) Inventor: Wei-Shui Wu, No. 97, Kuo-Chung Rd., Ta-Li, Taichung Hsien (TW)

( * ) Notice: Subject to any disclaimer, the term of this patent is extended or adjusted under 35 U.S.C. 154(b) by 474 days.

(21) Appl. No.: 11/925,564

(22) Filed: Oct. 26, 2007

(65) Prior Publication Data

US 2008/0045899 A1 Feb. 21, 2008

Related U.S. Application Data

(63) Continuation-in-part of application No. 11/211,451, filed on Aug. 26, 2005, now abandoned.

(51) Int. Cl.
*A61M 5/50* (2006.01)
(52) U.S. Cl. ...................................... 604/110
(58) Field of Classification Search ................. 604/110, 604/195
See application file for complete search history.

(56) References Cited

U.S. PATENT DOCUMENTS

| | | | | |
|---|---|---|---|---|
| 4,978,340 A * | 12/1990 | Terrill et al. | ................. | 604/195 |
| 5,531,705 A * | 7/1996 | Alter et al. | ................. | 604/195 |
| 5,820,605 A * | 10/1998 | Zdeb et al. | ................. | 604/195 |
| 5,968,019 A * | 10/1999 | Lee | ................. | 604/195 |
| 6,447,480 B1 * | 9/2002 | Brunel | ................. | 604/110 |
| 6,706,015 B2 * | 3/2004 | Bang | ................. | 604/110 |
| 2006/0089598 A1 * | 4/2006 | Wu | ................. | 604/110 |
| 2006/0229555 A1 * | 10/2006 | Wu | ................. | 604/110 |
| 2007/0060885 A1 * | 3/2007 | Wu | ................. | 604/110 |
| 2007/0078404 A1 * | 4/2007 | Wu | ................. | 604/198 |
| 2008/0058731 A1 * | 3/2008 | Wu | ................. | 604/218 |
| 2009/0234284 A1 * | 9/2009 | Wu | ................. | 604/110 |

* cited by examiner

*Primary Examiner*—Nicholas D Lucchesi
*Assistant Examiner*—Aarti B Berdichevsky
(74) *Attorney, Agent, or Firm*—Chun-Ming Shih

(57) ABSTRACT

A safety syringe device with separable needle stem by turning back includes a syringe tube, a push rod, a needle seat, a needle stem and a needle cap. The needle stem is attached to a bushing which is fitted to a core bit thereby fixing the needle seat at its position. The syringe tube and the needle seat that is screw combined are further tightly settled by dexterous positioning means. After finishing syringe, the needle sheet along with the needle stem is withdrawn and hidden in the syringe tube, the push rod can be broken at its brittle neck portion by tapping it against a breaking fringe formed around the syringe tube thereby leaving the needle seat and needle stem inside the syringe tube. By doing so, the used needle stem will never emerge out accidentally to puncture people's skin. The used syringe tube, push rod, needle seat and stem can be thrown away altogether to avoid restoring for reuse.

6 Claims, 9 Drawing Sheets

SAFETY SYRINGE DEVICE WITH SEPARABLE NEEDLE STEM BY TURNING BACK

RELATED APPLICATIONS

This application is a continuation-in-part of U.S. patent application Ser. No. 11/211,451 filed on Aug. 26, 2005 now abandoned.

BACKGROUND OF THE INVENTION

1. Field of the invention

The present invention relates to a safety syringe device with separable needle stem by turning back, and more particularly, to a syringe device whose used needle stem can be retrieved into the syringe tube, and with better friction force and packing state between its push rod and needle seat, and a structure easy for fabrication.

2. Description of the Prior Art

Keeping in pace with level up of the scientific and medical technology, people have been gradually more aware of importance of medical security for good health so that more and more attention is paid to disposal of used medical equipment. Improper treatment of the medical equipment, as that syringe needle which being intrusive to the human body, when being handled carelessly, may cause severe injury to both the patient and medical personnel.

Nowadays, repeated use of the syringe needle and accidental puncturing of the skin with the used syringe needle during disposing are most problematic. For solving these problems, the inventor of the present invention contrived several safety syringe devices and actually acquired some related patents. For the purpose of getting better and simpler structure, and even attaining optimums frictional force and packing state among components parts of the syringe device, he herein goes to great length of intensive research based on many years of experience acquired through professional engagement in the manufacturing of related products, with continuous efforts for improvement finally come up with an improved structure of the present invention.

SUMMARY OF THE INVENTION

The main object of the present invention is to provide a safety syringe device with a needle stem which being retrieval to the syringe tube after being completed syringing by turning back to separate in the manner breaking the exposed push rod at its neck of reduced diameter.

This safety syringe device with a simple, compact and easy to fabricate structure is composed of a syringe tube, a push rod, a needle seat, a needle stem and a needle cap.

Inside the syringe tube there forms a drug storing cavity provided with an inner threaded section at the front end thereof and an inner breaking fringe at the rear end thereof. The drug storing cavity is tapered forward to form a restriction space with reduced diameter. A needle hole is communicated with the drug storing cavity in the restriction space along whose inner surface is provided with a plurality of stop protuberances.

The push rod which being inserted into the syringe tube has a top pusher with reduced diameter on the top thereof, and several clogs are disposed around the lower outer circumference of the top pusher, and a ring packed tightly against the wall of the drug storing cavity in the syringe tube. Under the ring there is a neck portion with reduced diameter A core bit with reduced diameter set on the needle seat is extended out of the needle hole in the needle tube, and a bushing is fitted to the care bit and the needle stem, and finally covered by the needle cap. Then a passage is formed through the core bit, and an accommodation space is formed at the rear of the passage, several fixing blocks are provided on the surface of the accommodation space, between adjacent fixing blocks there is a barrier space to trap the clog of the push rod. Around the outer circumference of the needles seat there is provided with an outer thread section and a holding billet in correspondence with an inner thread section and the stop protuberances on the syringe tube.

With this structure, after the needle seat is attached to the top pusher on the push rod, and is moved to the needle hole, the outer thread section of the needle seat and the inner thread section of the syringe tube are combined together, and the holding billet is trapped between the stop protuberances of the syringe tube so as to tightly engage with each other. In the case of turning back the push rod reversely, the needle seat is moved down to separate from the needle hole. At the moment the neck of the push rod comes to be in contact with the breaking fringe around the syringe tube. The needle seat together with the attached needle stem will be left in the syringe tube by tapping the push rod against the breaking fringe to break its neck. At last insert the needle cap reversely into the needle hole.

BRIEF DESCRIPTION OF THE DRAWINGS

The drawings disclose the illustrative embodiments of the present invention which serve to exemplify the various advantages and objects hereof, and are as follows.

DETAILED DESCRIPTION OF THE PREFERRED EMBODIMENTS

Figure 1:
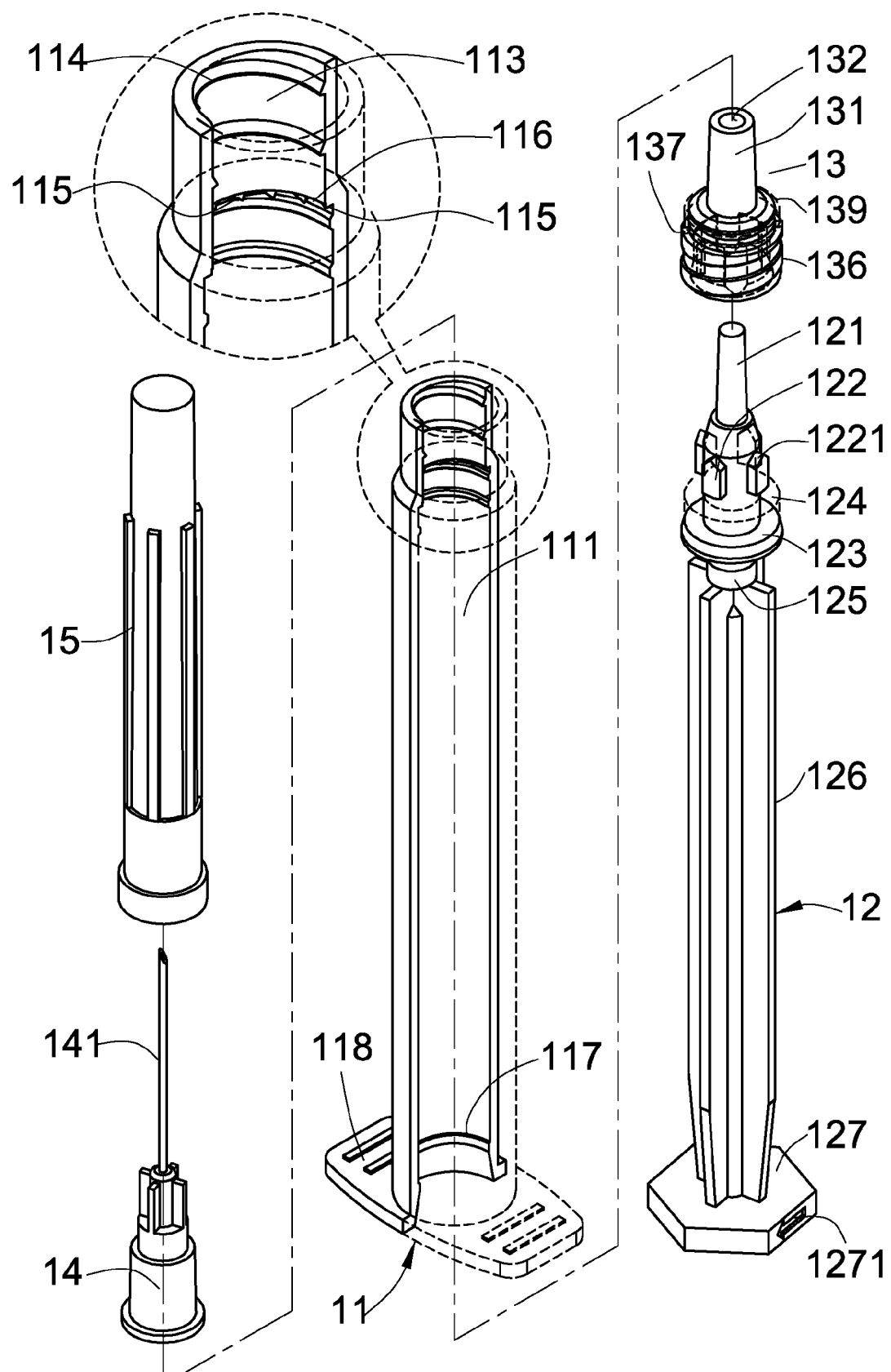
FIG. 1 is an exploded view of the safety syringe device according to the present invention.
Figure 2:
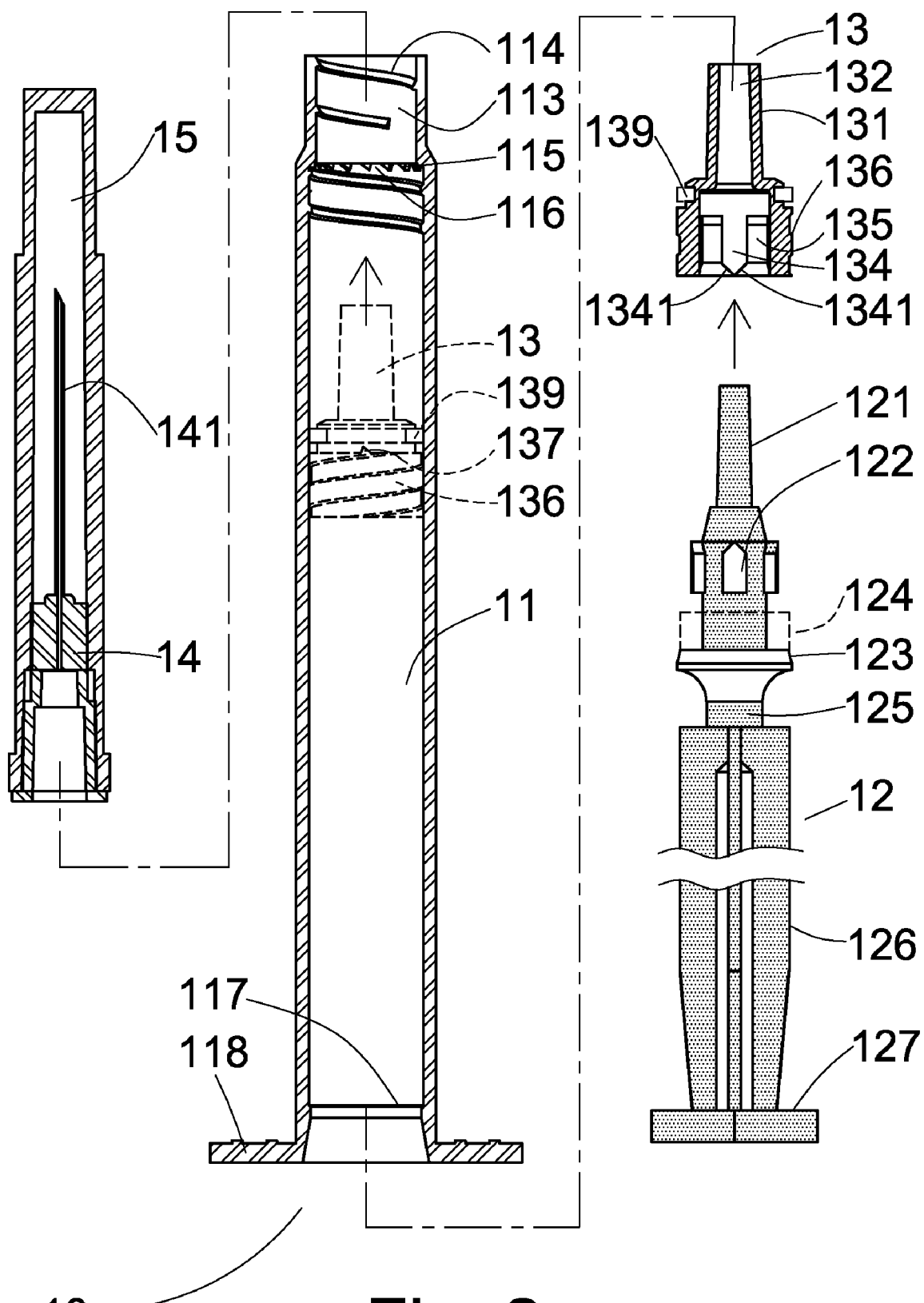
FIG. 2 is a cross sectional view of FIG. 1.
Figure 3:
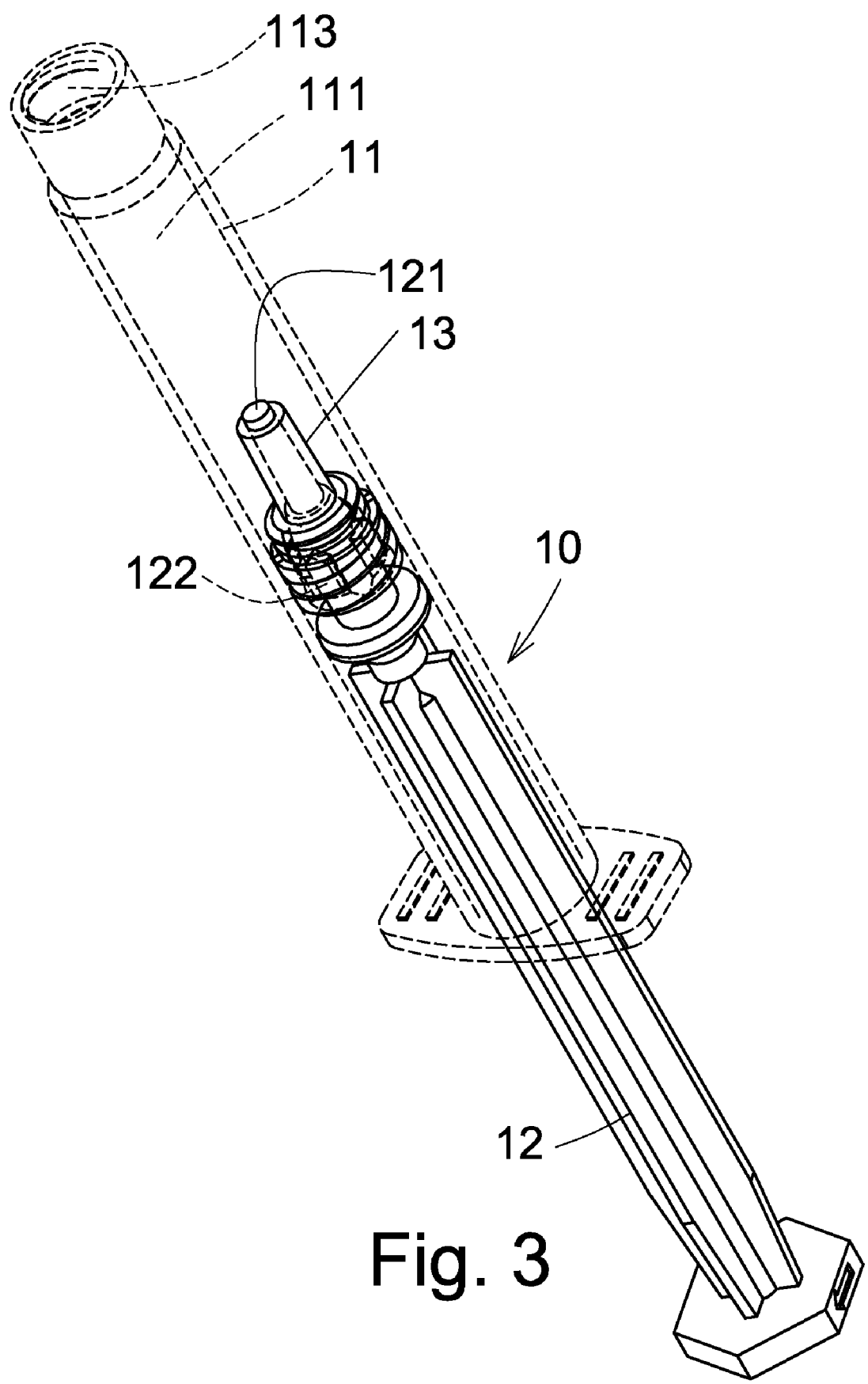
FIG. 3 is an illustrative view showing the push rod is inserted into the rear end of the syringe tube from the needle seat preparing to push forward.

Referring to FIGS. 1 and 2, the safety syringe device 10 of the present invention includes a syringe tube 11, a push rod 12, a needle seat 13, a needle stem 141 and a needle cap 15.

The syringe tube 11 whose structure is substantially identical to that of the syringe tube previously disclosed by the present inventor is essentially a cylindrical structure containing a drug storing cavity 111 in its center portion. A tapered restriction space 112 with a reduced diameter is formed at the front end of the cavity 111 with a needle hole 113 bored thereof so as to communicate with the drug storing cavity 111. The drug storing cavity 111 is provided with an inner square thread section 114 at its front end which is extended to the needle hole 113. In the restriction space 112 there are several triangle shaped stop protuberances 115 formed with an equal spacing around the inner circumferential surface thereof, and a recessed space 116 is formed between the adjacent stop protuberance 115 (see FIGS. 6 and 7). At the rear end inside the drug storing cavity 111 there are formed a breaking fringe 117 and a push plate 118 to be pushed with a thumb from outside.

The push rod 12 which is inserted into the syringe tube 11 has a top pusher 121 with reduced diameter on the top thereof, and several rectangular clogs 122 are disposed around the lower outer circumference of the top pusher 121. Each of the clogs 122 has a tilted guide surface 1221 formed at its front end inclining from the central portion to two sides, and each clog 122 further has a flange 123 formed around its lower portion and a ring 124 packed tightly against the wall of the drug storing cavity 111 in the syringe tube 11 between the clogs 122 and the flange 123. Under the flange 123 and ring 124 there is a neck portion 125 with a reduced diameter for holding the portion above the neck portion 125 within the syringe tube 11 by turning the push rod 12 after syringe is finished. The neck portion 125 is connected to several elongated ribs 126 under it, and a push plate 127 able to be pressed with a thumb is provided to the terminals of the ribs 126. The push plate 127 is formed into octagonal shape with an arrow head 1271 marked on two opposite sides.

A core bit 131 with reduced diameter set on the needle seat 13 is extended out of the needle hole 113 in the needle tube 11 after being surrounded with a ring 139 and positioned on a groove 138. A bushing 14 with similar shape is fitted to the core bit 131 to fix the needle seat 13 at its position. The needle stem 141 is attached to the bushing 14 either by insertion or adhesion. Then a passage 132 is formed through the core bit 131, and an accommodation space 133 (not shown) is formed at the rear of the passage 132 so as to communicate the needle seat 13 positioned at the restriction space 112 in the syringe tube 11, the accommodation space 133, the passage 132 and the needle stem 141 with one another; thereby the drug stored in the drug storing space 111 of the syringe tube 11 may be applied to the patient body through this route. Several fixing blocks 134 are provided on the surface of the accommodation space 133, and between adjacent fixing blocks 134 there is a barrier space 135. Each fixing block 134 is formed into a rectangular protruded shape in correspondence with the shape of the clog 122 of the push rod 12 and has a tilted guide surface 1341 inclined from the center to both sided formed at its bottom such that when assembling with the push rod 12, the clog 122 will be trapped into the barrier space 135 formed in the needle seat 13 and clogged thereat tightly through guiding of the guide surfaces 1221 and 1321 thus completing the assembly. Around the outer circumference of the accommodation space 133 in the needle seat 13 there is provided with an outer square thread section 136 and a holding billet 137 in correspondence with an inner square thread section 111 in the syringe tube 11 so as to combine the needle seat 14 and the syringe tube tightly by screwing. The triangle shaped holding billet 137 can be trapped into the recessed space 116 formed between two adjacent stop protuberances 115 so as to hold the needle seat 14 in the stationary state.

The cone shaped needle cap 15 can be used to cover the bushing 14 sticking out of the needle hole 112 of the syringe tube 11 to protect it so as to avoid puncturing the people's skin with the emerged needle stem 141.

Figure 4:
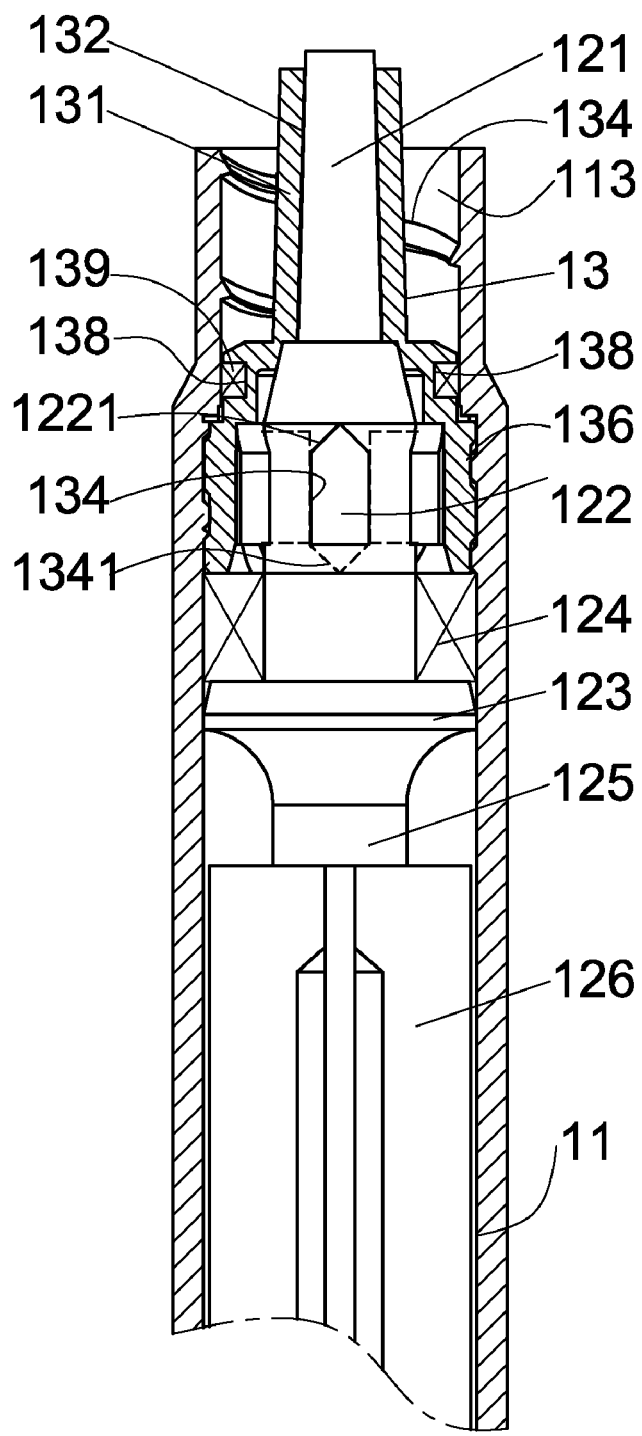
FIG. 4 is a cross sectional view showing the push rod which is inserted into the syringe tube is passing through the needle hole.

Referring to FIG. 4, with the aforesaid structure, when using the safety syringe device 10, at first the needle seat 13 is placed in the drug storing cavity 111 of the syringe tube 11, and the push rod 12 is pushed forward form the rear of the needle seat 13, then the clog 122 is trapped into the corresponding barrier space 135 formed between two adjacent fixing blocks 134 so as to complete the assembly work. By continuously pushing the push rod 12 to bring the needle seat 13 forward until the core bit 131 passes through the needle hole 113 of the syringe tube 11, the outer thread section 136 of the needle seat 13 is combined with the inner thread section 114 of the syringe tube 11 so that the needle seat 13 can advance by turning as shown in FIG. 4.

Figure 5:
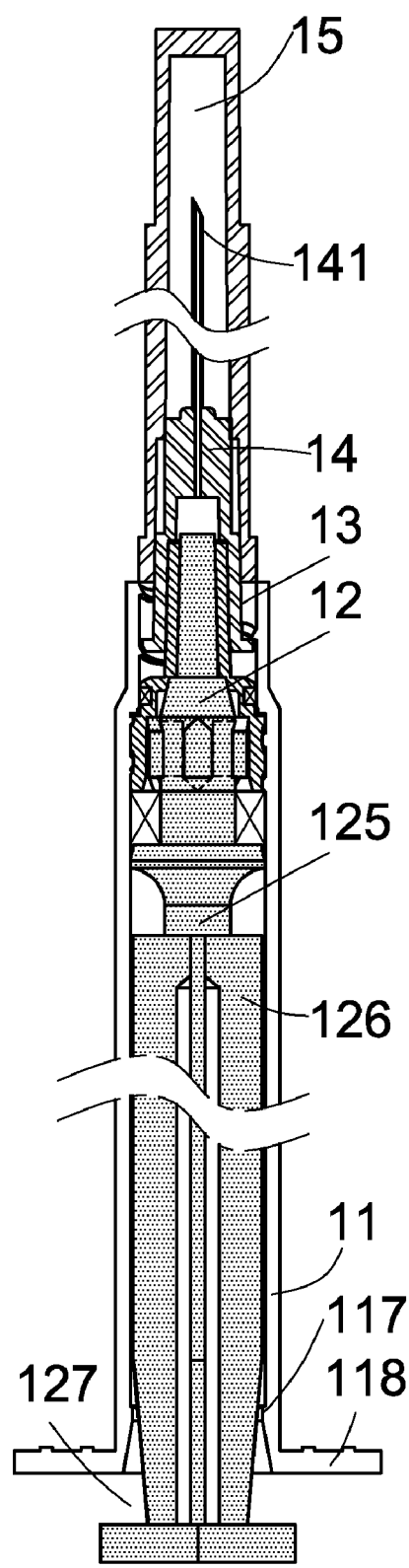
FIG. 5 is a cross sectional view showing the needle cap is covered on the needle stem so as to protect it.
Figure 6:
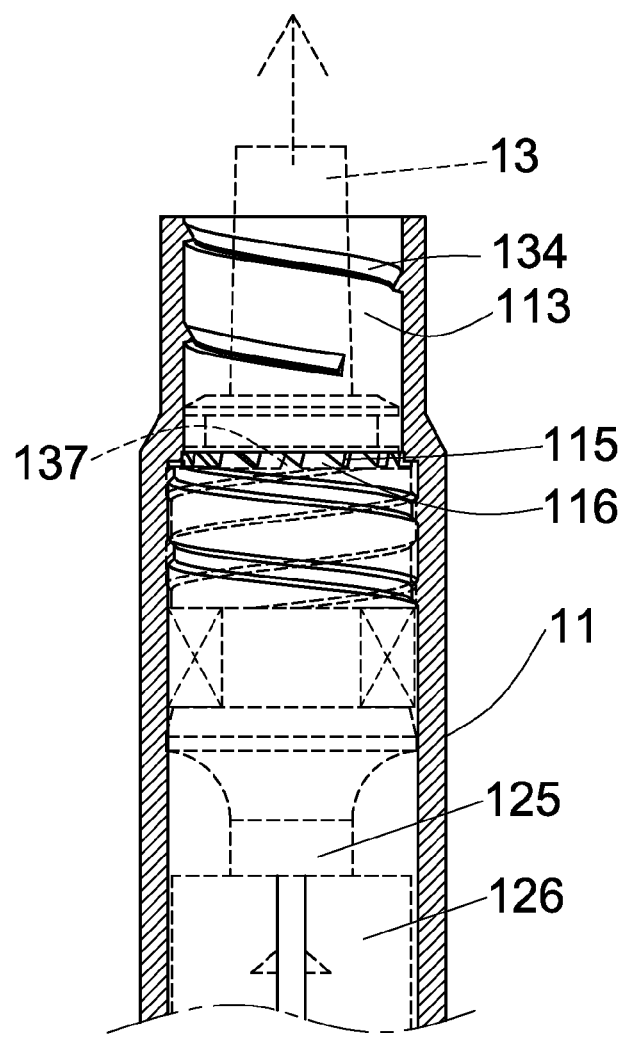
FIG. 6 is a factionary view of FIG. 4 for illustration of the operation of the syringe device.
Figure 7:
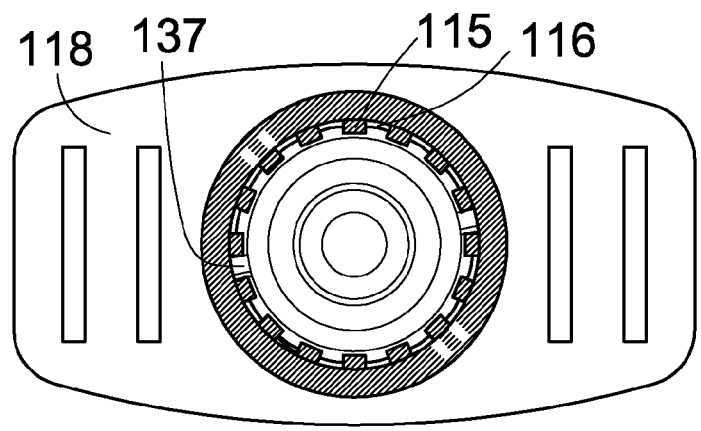
FIG. 7 is a top view looked down from the top of FIG. 6.

Referring to FIG. 5 through FIG. 7, as soon as the holding billet 137 is trapped into the recessed space 116 formed between two adjacent stop protuberances 115 of the syringe tube 11, a ring 139 around the needle seat 13 is hindered in the restriction space 112 of the syringe tube 11 and packing against the wall of the syringe tube 11 along with the ring 124 on the push rod 12 so as to ensure the drug storing cavity 111 in a perfect sealed state. Next, let the core bit 131 on the needle seat 13 emerging out of the needle hole 112 together with the bushing 14, and then cover it with the needle cap 15 (see FIG. 5).

Figure 8:
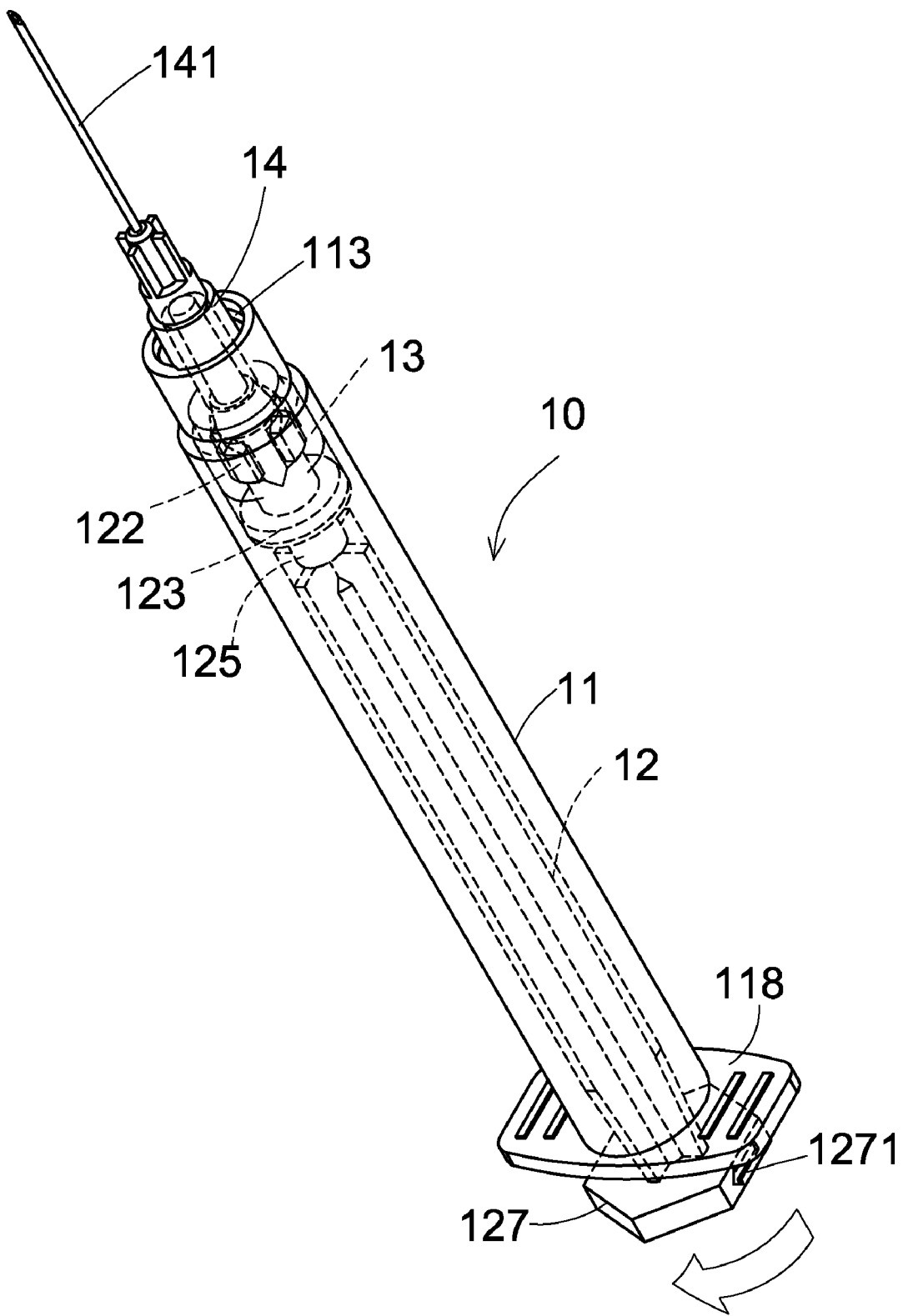
FIG. 8 is an illustrative view showing the push rod is turned in the reverse direction to bring down the needle seat for detaching the holding billet from being held.
Figure 9:
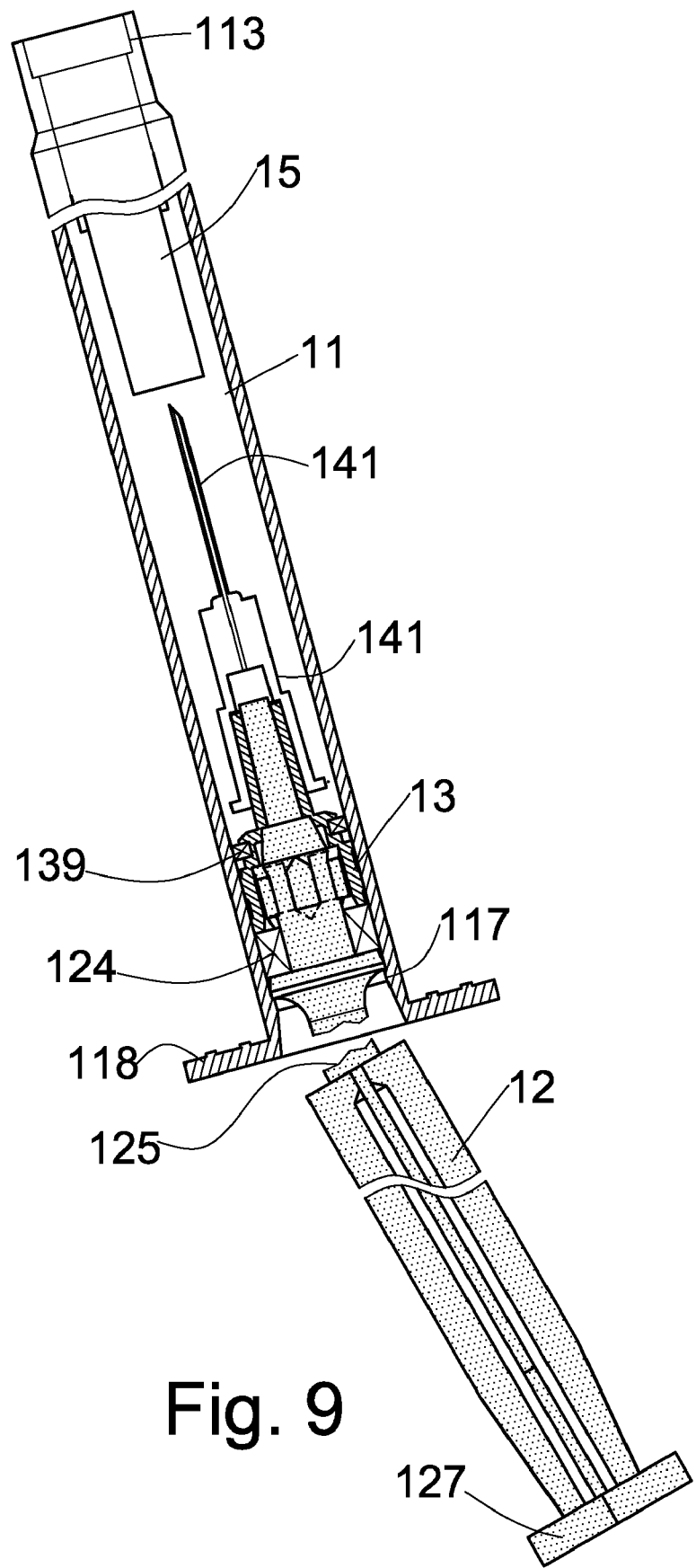
FIG. 9 is an illustrative view showing the needle seat and the needle stem are left in the syringe tube after breaking the push rod neck, and the needle cap is reversely inserted into the needle hole of the syringe tube.

Referring to FIGS. 8 and 9, when the user intends to draw the drug solution into the syringe device, the operation manner is the same as that is done with a conventional syringe device, by taking off the needle cap 15 and soaking the needle stem 141 in the drug solution (not shown), the push rod 12 is drawn up to suck the drug solution into the drug storing cavity 111. Since the needle seat 13 can be firmly affixed to the syringe tube 11 at its position by means of the outer thread section 136 and the holding billet 137 without being affected by straight reciprocating motion of the push rod 12. After completing the syringe, the push rod 12 continues to go forward and traps its clog 122 into the corresponding barrier space 135 of the needle seat 13, afterwards turning the push rod 12 in the reverse direction together with the needle seat 13 to liberate its holding billet 137 from the recessed space 116 (see FIG. 8). As soon as the entire needle seat 13 is liberated from the inner thread section 114 of the syringe tube 11, it is hidden in the syringe tube 11 with the needle stem 141, and as soon as the neck portion 125 of the push rod 12 retreats to the place where the breaking collar 117 with slightly smaller inner diameter than the outer diameter of the needle seat 13, is formed around the drug storing cavity 111, the push rod 12 is broken at its brittle neck portion 125 by tapping it repeatedly against the breaking collar 117 (see FIG. 9) thereby leaving the needle seat 113 and stem 141 in the syringe tube 11, afterwards the needle cap 15 is reversely inserted into the needle hole 13 for disposal.

Figure 10:
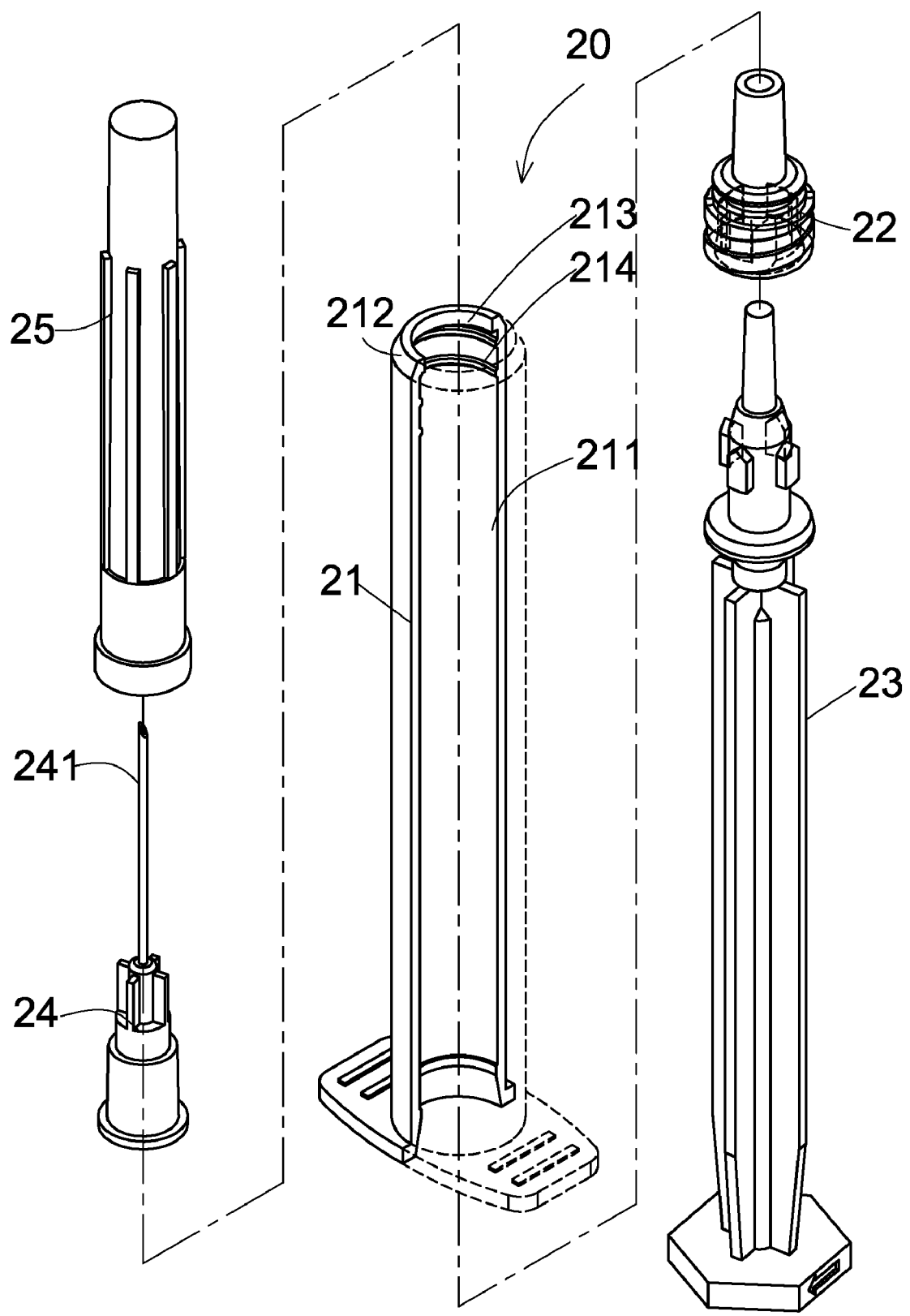
FIG. 10 is an exploded view of the syringe device in another embodiment of the present invention.
Figure 11:
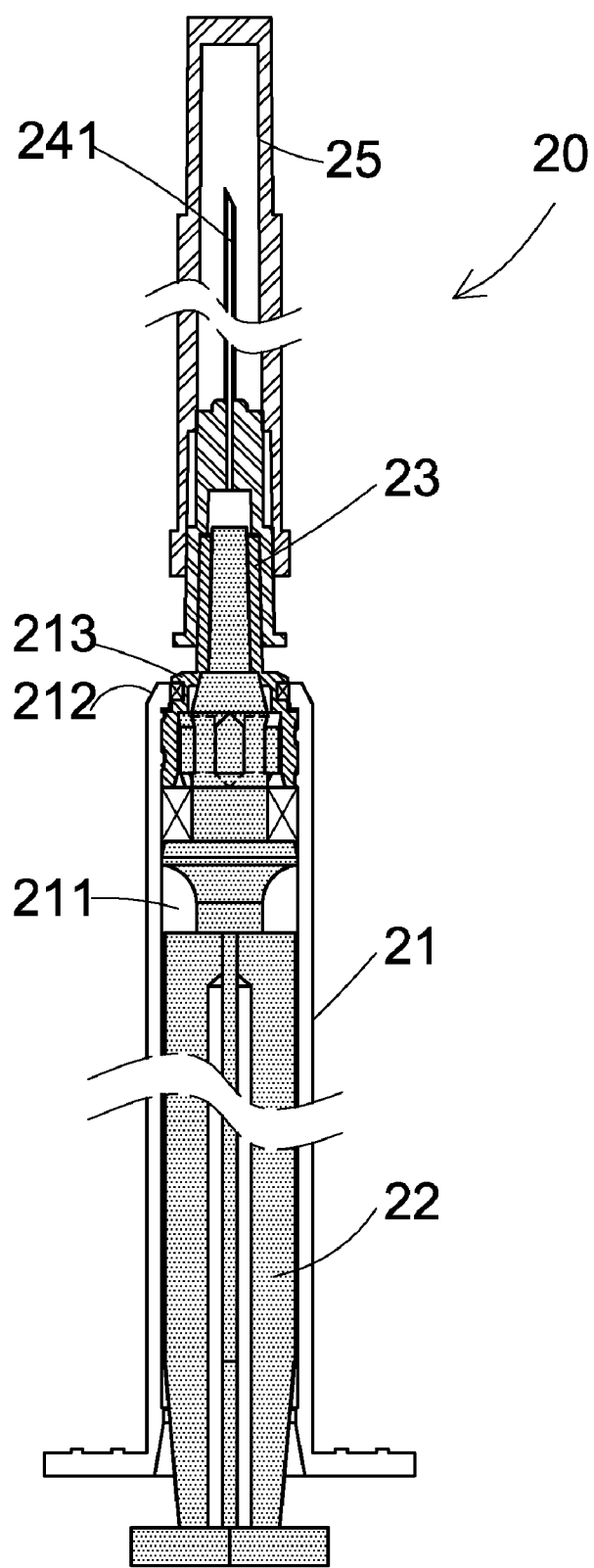
FIG. 11 is a cross sectional view of the syringe device shown in FIG. 10

Another embodiment of the present invention is shown in FIGS. 10 and 11 wherein a safety syringe device 20 also comprises a syringe tube 21 a push rod 22, a needle seat 23, a needle stem 241 and a needle cap 25. The only difference with the first embodiment lies in that the distance between he restriction space 212 and the needle hole 213 in the syringe tube 21 is shorter than that of the first embodiment. An inner square thread section 214 is provided in the front portion of a drug storing cavity 211, e.g. at a position proximate to the needle hole 213. All of the component parts, the push rod 22, the needle seat 23, the needle stem 241 and the needle cap 25 are identical to those used in the first embodiment in characters, structure arrangement and performance.

It emerges from the above description that the invention has several noteworthy advantages, in particular:

1. The used needle stem 141 is securely accommodated in the syringe tube 11 without the fear of emerging out accidentally to puncture people's skin. The used syringe tube 11, push rod 12, needle seat 13 and needle stem 141 can not be restored for reuse thereby assuring medical security.

2. The needle seat 13 and the syringe tube 11 are securely combined together by engagement of the outer and inner thread sections. A better yield in molding the syringe tube 11 and the needle seat 13 can be ensured.

3. The dexterously designed stop protuberances 115 in the restriction space 112, and the recessed space 116 between the adjacent two stop protuberances 115 to trap the holding billet 137 provide a proper frictional and occlusive force between the needle seat 13 and the syringe tube 11 to protect them from accidental excursion. Provision of the rings 139,124 for the needle seat 13 and the push rod 12 enhances perfect sealing for the drug storing cavity 111 free from the fear of leaking the drug solution.

Although the present invention has been described in terms of the presently preferred embodiments, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

What is claimed is:

1. A safety syringe device with a separable needle stem by turning back, comprising:

a syringe tube containing a drug storing cavity with an inner thread section formed at a front end thereof, a tapered restriction space with a reduced diameter formed at the front end of the drug storing cavity, a needle hole bored through the restriction space to communicate with the drug storing cavity, and several stop protuberances provided around the inner circumferential surface of the restriction space;

a push rod inserted into the syringe tube, having a top pusher with reduced diameter on the top thereof, and several clogs disposed around the lower outer circumference of the top pusher, a ring packed tightly against the wall of the drug storing cavity in the syringe tube, and a neck portion with reduced diameter formed under the ring; and a needle seat installed on the restriction space in the syringe tube, having a core bit with reduced diameter set on the front of the needle seat and extended out of a needle hole of the needle tube, the core bit being connected with a needle stem and covered with a needle stem and covered with a needle cap, wherein a passage is formed through the center of the core bit and an accommodation space is formed at the rear of the passage, several fixing blocks are provided on the surface of the accommodation space, a barrier space is formed between the adjacent fixing blocks to trap the clogs formed around the top pusher, around the outer circumference of the accommodation space in the needle seat there is provided with an outer thread section and a holding billet in correspondence with the inner thread section in the syringe tube to combine tightly with each other while the holding billet is engaged with the stop protuberance of the syringe tube.

2. The safety syringe device of claim 1, wherein the inner thread section of the syringe tube and the outer thread section of the needle seat are formed of square thread.

3. The safety syringe device of claim 1, wherein the plurality of stop protuberances are equally spaced triangle shaped members, whereas the holding billet is also triangle shaped so as to be trapped into the recessed spaced formed between the two adjacent stop protuberances.

4. The safety syringe device of claim 1, wherein each of the clogs of the push rod has a tilted guide surface formed at its front end inclining from the central portion to two sides, whereas each of the fixing blocks of the needle seat also has a tilted guide surface formed at he bottom thereof being inclined from the center to both sides in correspondence with the clog of the push rod.

5. The safety syringe device of claim 1, wherein a breaking fringe is formed at the rear end inside the drug storing cavity, the breaking fringe has a smaller inner diameter than the outer diameter of the needle seat, the push rod is broken at its brittle neck portion by tapping it repeatedly against the breaking fringe thereby leaving the needle seat and the needle stem in the syringe tube.

6. The safety syringe device of claim 1, wherein the needle stem is attached to a bushing which being fitted to a core bit thereby fixing the needle seat at its position.

* * * * *